US007323200B2

(12) United States Patent
Chmura et al.

(10) Patent No.: US 7,323,200 B2
(45) Date of Patent: Jan. 29, 2008

(54) CALCIUM FORTIFIED, SOY BASED, INFANT NUTRITIONAL FORMULAS

(75) Inventors: James N. Chmura, Canal Winchester, OH (US); Kent L. Cipollo, Westerville, OH (US); Louis I. Ndife, Columbus, OH (US); Karin M. Ostrom, Marlborough, CT (US)

(73) Assignee: Abbott Laboratories, Abbott Park, IL (US)

( * ) Notice: Subject to any disclaimer, the term of this patent is extended or adjusted under 35 U.S.C. 154(b) by 942 days.

(21) Appl. No.: 10/642,870

(22) Filed: Aug. 18, 2003

(65) Prior Publication Data

US 2005/0042329 A1 Feb. 24, 2005

(51) Int. Cl.
*A23L 1/20* (2006.01)
(52) U.S. Cl. .................... 426/46; 426/74; 426/431; 426/634; 426/801
(58) Field of Classification Search ................ 426/46, 426/634, 74, 431, 801
See application file for complete search history.

(56) References Cited

U.S. PATENT DOCUMENTS

| 2,732,395 | A |   | 1/1956 | Bolley et al. |
| 3,733,207 | A |   | 5/1973 | McCabe et al. |
| 3,736,147 | A |   | 5/1973 | Lacobucci et al. |
| 4,072,670 | A |   | 2/1978 | Goodnight et al. |
| 4,642,236 | A |   | 2/1987 | Friend et al. |
| 4,697,004 | A |   | 9/1987 | Puski et al. |
| 5,248,765 | A |   | 9/1993 | Mazer et al. |
| 5,248,804 | A |   | 9/1993 | Nardelli et al. |
| 5,270,450 | A |   | 12/1993 | Westfall et al. |
| 6,313,273 | B1 | * | 11/2001 | Thomas et al. ............. 530/378 |
| 6,808,736 | B2 | * | 10/2004 | Rangavajhyala et al. ... 426/598 |
| 2001/0007868 | A1 |   | 7/2001 | Facchini |
| 2001/0018197 | A1 |   | 8/2001 | Wong et al. |
| 2001/0123090 |    |   | 9/2002 | Wong et al. |
| 2002/0127288 | A1 |   | 9/2002 | Wong et al. |
| 2004/0062820 | A1 | * | 4/2004 | Lasekan et al. ............. 424/682 |
| 2004/0062849 | A1 | * | 4/2004 | Lien et al. .................. 426/629 |

FOREIGN PATENT DOCUMENTS

| EP | 380343 | 1/1990 |
| GB | 1574110 | 9/1980 |
| GB | 2180241 | 3/1987 |
| JP | 50130800 | 10/1975 |
| JP | 7060635 | 3/1995 |
| WO | WO 9830681 | 7/1998 |
| WO | WO 0210322 | 2/2002 |

OTHER PUBLICATIONS

Pallaf et al., Dietary phytate reduces magnesium bioavailability in growing rats, Nutr Res 1998; 18:1029-1037.
Lonnerdal B: Nutritional aspects of soy formula, Acta Paediatr Suppl 1994;402:105-108.
Quinlan et al, The relationship between stool hardness and stool composition in breast and formula fed infants, JPGN 1995; 20:81-90.
Lasekan et al, Growth of newborn, term infants fed soy formula for one year. Clin Pediatr 1999; 38:563-571.
Ling and Weaver, QJM-Monthly Journal of the Assoc. of Physicians, vol. 90 (1997).
Churella HR, Vivian V. The effect of phytic acid in soy infant formulas on the availability of minerals for the rat FASEB J 1976; 35:744.
Graf E, Eaton JW. Effects of phytate on mineral bioavailability in mice. J Nutr 1984; 1145:1192-1198.
Ziegler et al. Effect of phytate reduction on mineral absorption from soy-based infant formula. Am J Clin Nutr 1990; 51:528.
Lynch et al., Inhibitory effect of a soybean-protein-related moiety on iron absorption in humans., Am J Clin Nutri 1994 60:567-572.
Reddy et al., The influence of different protein sources on phytate inhibition on nonheme-iron absorption in humans. Am J Clin Nutr 1996; 63:203-207.
Miyazawa et al., Phytate breakdown and apparent absorption of phosphorus, calcium, and magnesium in germfree and conventionalized rats. Nutr Res 1996; 16:603-613.
Shen et al., An inositol phosphate as a calcium absorption enhancer in rats. J Nutr Biochem 1998; 9:298-301.
Lopez et al., Intestinal fermentation lessens the inhibitory effects of phytic acid ion mineral utilization in rats. J Nutr 1998; 128:1192-1198.
Lonnerdal et al., Effect of reducing the phytate content and of partially hydrolyzing the protein in soy formula on zinc and copper absorption and status in infant rhesus monkeys and rat pups. Am J Clin Nutr 1999; 69:490-496.
Van Dael et al., The effect of dephytinization on calcium, copper, iron, manganese, zinc absorption from a soy infant formula. JPGN 1999; 28:595.

(Continued)

*Primary Examiner*—Helen Pratt
(74) *Attorney, Agent, or Firm*—William J. Winter; Sandra E. Weida

(57) ABSTRACT

Disclosed are calcium fortified, soy-based, infant nutritional formulas, including powder, liquid, or concentrate embodiments comprising per 100 kcal of formula (A) lipid, preferably up to about 8.0 g, (B) carbohydrate, preferably from about 8.0 g to about 16.0 g, (C) phytase-treated soy protein, preferably up to about 3.5 g and (D) calcium, preferably up to about 90 mg of calcium; wherein the nutritional formula is an infant formula having a calcium to lipid weight ratio of from about 0.002 to about 0.020, and wherein the formula contains not more than about 8.4 mg phytic acid per 100 kcal of formula. It has been found that these calcium-fortified, phytase-treated, soy-based, nutritional formulas provide for softer stools in infant populations, especially as compared to infants fed with other soy-based formulas including commercial soy formulas as well as soy based formulas derived from dephytinization methods other than phytase treatment, e.g., ion exchange.

6 Claims, No Drawings

OTHER PUBLICATIONS

Kennedy et al., Double-blind, randomized trial of a synthetic triacylglycerol in formula-fed infants: effects on stool biochemistry, stool characteristics and bone mineralization, Am J Clin Nutr 1999; 70:920-7.
Reddy, et al, Adv. Food Res., 28:1-92 (1982).
Cheryan, CRC Crit. Rev Food Sci Nutri 13:297-335 (1980).
McKinney, et al, J Biol Chem, 178:117-132 (1949).
DeRham and Jost., J. Food Sci, 44:596-600 (1979).
Brooks and Morr, J. Food Sci., 47:1280-1282 (1982).
Han and Wilfred, J. Agric Food Chem, 36:259-262 (1988).
Spivey Fox MR, Tas SH: Antinutritive effects of phytate and other phophorylated derivatives, Nutr Toxicol 3:59-96 (1989).
Hurrell et al, ; A comparison of iron absorption in adults and infants consuming identical infant formulas, Br J Nutr 79:31-36 (1998).
Davidson et al., Iron bioavailability studies in infants-the influence of phytic acid and ascorbic acid in infant formulas based on soy isolate, Peditr Res 36; 6:816-822 (1994).
Hurrell et al., Soy protein, phytate, and iron absorption in humans, Am J Clin Nutr 1992; 56:573-578.
Lynch et al., Inhibitory effect of a soybean-protein-related moiety on iron absorption in humans. Am J Clin Nutr 1994; 60:567-572.
Rimach et al., Effect of phytic acid and microbial phytase on Cd accumulation, Zn status, and apparent absorption of Ca, P, Mg, Fe, Zn, Cu and Mn in growing rats. Am Nutr Metab 1995; 39:361-370.
Beate et al., Formula Tolerance in Postbreastfed and exclusively formula-fed infants, Pediatrics vol. 103 No. 1 Jan 1999.
Nowicki MJ, Bishop PR, Organic Causes of constipation in infants and children, Ped Annals, 28:5/May 1999.
Editorial, The fate of fat in the infant's colon, QJ Med 1997; 90:553-555.
Forsyth et al., Randomized controlled study of the effect of long chain polyunsaturated fatty acid supplementation on stool hardness during formula feeding, Archives of Disease in Childhood, 1999, vol. 81, N# (Sep.) 253-256.
Lloyd et al., Formula tolerance in postbbreastfed and exclusively formula-fed infants, Pediatrics, 1999; 103, N1 (Jan.), PE71-E76.
Morley et al., Infant feeding and maternal concerns about stool hardness, Child: care, health and development, Jul. 8, 1997, 23; 6:475-478.

* cited by examiner

CALCIUM FORTIFIED, SOY BASED, INFANT NUTRITIONAL FORMULAS

TECHNICAL FIELD

The present invention relates to calcium fortified, soy-based, infant formulas that provide infants with softer stool formation and reduced incidence of constipation.

BACKGROUND OF THE INVENTION

There are many different infant nutritional formulas that are commercially available or otherwise known in the infant formula art. These infant formulas comprise a range of nutrients to meet the nutritional needs of the growing infant, and typically include lipids, carbohydrates, protein, vitamins, minerals, and other nutrients helpful for optimal infant growth and development. These formulas are typically derived in part from cows milk or from soy protein isolates or concentrates.

Soy-based infant formulas are well known and readily available from a number of commercial sources, including Similac® Isomil® Advance® Infant Formulas available from Ross Products Division, Abbott Laboratories, Columbus, Ohio. These soy-based formulas are prepared especially for infants with feeding problems such as fussiness, gas, and spit-up, as well as for infants whose parents choose a non-milk-based formula as a first feeding or as a supplement to breastfeeding. These soy-based formulas are especially helpful for those infants with allergies or sensitivities to cow's-milk protein, and for those infants with disorders for which lactose from cow's milk should be avoided.

Some soy-based infant formulas, however, have historically had a tendency to promote harder stools in some infants as compared to breast-fed infants, which can then lead to constipation in some infants. This can be especially problematic for soy-based infant formulas that are iron and calcium fortified, since it is well known that both iron and calcium can further promote harder stool formation. These nutrients, however, are important for the optimal growth and development of infants, and thus for formula fed infants must be provided in either the formula or in other dietary or supplemental sources.

It is therefore an object of the present invention to formulate a calcium fortified, soy-based infant formula that provides nutrition and softer stool formation. It is a further object of the present invention to provide such a formula that reduces the incidence of constipation in infants fed a soy-based formula. It is a further object of the present invention to provide such benefits from calcium-fortified infant formula, and further to provide such benefits from a calcium and iron fortified infant formula.

These and other objects of the present invention will be described or otherwise suggested in greater detail hereinafter.

SUMMARY OF THE INVENTION

The present invention is directed to calcium fortified, soy based, nutritional formulas for infants, said formulas including liquid embodiments comprising (A) up to about 5.4% by weight of lipid, (B) from about 5.4% to about 10.8% by weight of carbohydrate, (C) up to about 2.4% by weight of phytase-treated soy protein, and (E) up to about 600 mg of calcium per liter of formula, wherein the formula is an infant formula and has a calcium to lipid weight ratio of from about 0.002 to about 0.020, and the formula contains not more than about 0.3%, preferably zero percent, phytic acid by weight of the phytase-treated protein.

The present invention is also directed to calcium fortified, soy based, nutritional formulas for powder, liquid, or concentrate product forms. These nutritional formulas comprise per 100 kcal (A) lipid, preferably up to about 8.0 g, (B) carbohydrate, preferably from about 8.0 g to about 16.0 g, (C) phytase-treated soy protein, preferably up to about 3.5 g and (D) calcium, preferably up to about 90 mg of calcium; wherein the nutritional formula is an infant formula having a calcium to lipid weight ratio of from about 0.002 to about 0.020, and wherein the formula contains not more than about 8.4 mg phytic acid per 100 kcal of formula.

It has been found that the soy-based formulas of the present invention provide for an increased incidence of softer stool formation in infants, provided that the weight ratio of the total calcium to lipids is from about 0.002 to about 0.020, and provided that the protein component comprises a phytase-treated protein that provides the composition with not more than 0.3%, preferably zero percent, of phytic acid by weight of the phytase-treated protein. It has been found that by selecting a phytase-treated soy protein having a low phytic acid content and by selecting a calcium to lipid ratio as defined herein, that infant stool consistency as defined herein can be optimized or improved over other more conventional soy-based formulas, and even over other soy-based formulas having low phytic acid concentrations derived from manufacturing methods such as ion exchange or other similar dephytinization methods, i.e., methods other than phytase treatment.

DETAILED DESCRIPTION OF THE INVENTION

The calcium-fortified, soy-based, infant formulas of the present invention comprise as essential elements certain nutrient components, including a phytase-treated soy protein, lipid and carbohydrate nutrients, and calcium fortification in a defined relationship with the lipid component. These and other essential or optional characteristics of the nutritional compositions of the present invention are described in greater detail hereinafter.

The term "infant" as used herein, refers generally to children less than about 2 years of age, most typically less than about 1 year of age, and the term "infant formula" as used herein refers to the compositions of the present invention and is meant to limit the use thereof to such infants to meet their sole, primary, or supplemental nutritional needs.

The term "calcium-fortified" as used herein refers to the infant formulas of the present invention, wherein the formula as a ready-to-feed product, or as a powder or concentrate when diluted or reconstituted prior to use, contains from about 10 mg to about 600 mg of calcium per liter of formula. In this context, the calcium-fortification is calculated in terms of elemental calcium, and includes both added calcium and calcium that is inherent in other added nutrients or formula components.

The term "phytic acid" as used herein refers generally to inositolhexaphosphoric acid, but in the context of the present invention, is also meant to include inositolpentaphosphoric acid, inositoltetraphosphoric acid, inositoltriphosphoric acid, inositoldiphosphoric acid, inositolmonophosphoric acid, and so forth, and also includes salts and molecular complexes thereof. For purposes of defining phytic acid concentrations of the infant formulas of the present invention, phytic acid concentrations can be determined in accordance with the method disclosed by, Sandberg, A., and Ahderinne, R., *Phytic Acid Measurement Method*, Journal of Food Science, 52:547 (1986).

The term "lipid" as used herein, unless otherwise specified, means fats, oils, and combinations thereof.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The infant formulas of the present invention, including the many embodiments described herein, can comprise, consist of, or consist essentially of the essential elements and limitations of the invention described herein, as well as any additional or optional ingredients, components, or limitations described herein or otherwise useful in infant nutritional formula applications.

I. NUTRIENTS

The infant formulas of the present invention comprise sufficient types and amounts of nutrients to help meet the sole, primary, or supplemental nutritional needs of the infant. These nutrients include lipids, proteins, and carbohydrates, and preferably further comprise vitamins, minerals (in addition to the calcium component described hereinafter), or combinations thereof.

The infant formulas of the present invention comprise lipid, carbohydrate, and protein nutrients at concentration ranges that vary depending on variables such as product form. These nutrient concentrations of the infant formulas of the present invention are described below in Table 1.

TABLE 1

Infant Formula Nutrients

| Nutrient | Range | g/100 kcal | g/100 g powder | g/L as fed |
|---|---|---|---|---|
| Carbohydrate | Preferred | 8-16 | 30-90 | 54-108 |
| | More preferred | 9-13 | 45-60 | 61-88 |
| Lipid | Preferred | 3-8 | 15-35 | 20-54 |
| | More preferred | 4-6.6 | 25-25 | 27-45 |
| Protein | Preferred | 1-3.5 | 8-17 | 7-24 |
| | More preferred | 1.5-3.4 | 10-17 | 10-23 |

Many different sources and types of carbohydrates, lipids, proteins, minerals and vitamins are known and can be used in the nutritional compositions of the present invention, provided that such nutrients are compatible with the essential and other added ingredients in the selected formulation, are safe and effective for their intended use, and do not otherwise unduly impair product performance.

Carbohydrate

The infant formulas of the present invention comprise carbohydrate nutrients, which may include hydrolyzed or intact, naturally and/or chemically modified, starches sourced from corn, tapioca, rice or potato, in waxy or non-waxy forms. Other non-limiting examples of suitable carbohydrate sources for use herein include hydrolyzed cornstarch, maltodextrin, glucose polymers, sucrose, corn syrup, corn syrup solids, glucose, fructose, high fructose corn syrup, and combinations thereof. The carbohydrates component may comprise lactose or may be substantially free of lactose.

Lipid

The infant formulas of the present invention also comprise as an essential element a lipid nutrient, which may include coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oils, and combinations thereof.

Other suitable lipids or related materials suitable for use in the infant formulas include those that provide specific fatty acids, including arachidonic acid, docosahexaenoic acid, or mixtures thereof. These materials are known to provide beneficial effects in infants such as enhanced brain and vision development, descriptions of which are set forth in U.S. Pat. No. 5,492,938 (Kyle et al.), which descriptions are incorporated herein by reference. Non-limiting examples of suitable sources of arachidonic acid and docosahexaenoic acid include marine oil, egg-derived oils, fungal oil, algal oil, and combinations thereof.

The lipid component of the infant formulas of the present invention may comprise one or more of arachidonic acid, docosahexaenoic acid, or combinations thereof, alone or in further combination with linoleic acid and linolenic acid. Arachidonic acid concentrations preferably range up to about 2.0%, more preferably from about 0.2% to about 1.0%, even more preferably from about 0.35% to about 0.9%, and most preferably from about 0.4% to about 0.5%, by weight of the total fatty acids in the formula. Docosahexaenoic acid concentrations preferably range up to about 1.0%, more preferably from about 0.1% to about 1.0%, and even more preferably from about 0.14% to about 0.36%, by weight of the total fatty acids in the formula. Linoleic concentrations preferably range up to about 30%, more preferably from about 10% to about 30%, and even more preferably from about 15% to about 20%, by weight of the total fatty acids in the formula. Linolenic acid concentrations preferably range up to about 4%, more preferably from about 1.5% to about 4%, even more preferably from about 2% to about 3%, and even more preferably from about 2.2% to about 2.6%. These lipid materials are described in U.S. Pat. No. 6,495,599 (Auestad et al.), which description is incorporated herein by reference.

Protein

The infant formulas of the present invention also comprise as an essential element a soy protein isolate derived in whole or in part, preferably in whole, from any phytase treatment method that is known or otherwise suitable for effectively reducing inherent phytic acid concentrations in the resulting protein isolate so that the isolate, when formulated into the infant formulas of the present invention, provides a low-phytic acid formulation as defined herein.

In this context, a "low-phytic acid" formulation is one in which the soy protein used in the formulation contains not more than about 0.3%, preferably not more than about 0.2%, even more preferably not more than 0.05%, and even more preferably zero percent, of phytic acid by weight of the soy protein isolate. By contrast, many conventional soy protein isolates are not typically dephytinized, and thus generally contain from about 1.2% to 4.0% phytic acid by weight of the isolates. For purposes of defining various powder, liquid, and concentrated formula embodiments of the present invention, a "low-phytic acid" formulation preferably includes any such formula comprising per 100 kcal not more than 8.4 mg, preferably not more than 2.8 mg, more preferably not more than 1.4 mg, and even more preferably zero mg, of phytic acid.

It is well known that phytic acid, which is naturally present in soybeans, tends to bind to and reduce the bioavailability of nutrients such as divalent cations in the gastrointestinal tract of humans. It has therefore been the focus of much research over the years to develop methods of making low-phytic acid, soy protein isolates, to thus provide a protein source for a more nutritious infant formulation. Examples of such methods developed over the years include phytase treatment methods such as those described in U.S. patent application 20020127288 A1 (Wong et al.), ion exchange methods such as those described in U.S. Pat. No. 5,248,804 (Nardelli et al.), both descriptions of which are incorporated herein by reference. Other methods of making low-phytic acid protein isolates are referenced in or otherwise described, for example, in European Patent Application 0 380 343 A2 (Simell et al.).

For purposes of defining the infant formulations of the present invention, the protein isolate component may be derived from any phytase treatment method that is known or otherwise suitable for producing a low-phytic acid protein isolate, provided that the method clearly involves the use of phytase or other similar-functioning enzyme to reduce phytic acid concentrations, and provided that the resulting phytic acid concentration in the resulting infant formula falls within the low-phytic acid concentration ranges as defined herein.

The infant formulas of the of the present invention include formula embodiments comprising phytase-treated soy protein prepared by treating a soy protein material with a phytase-containing enzyme, and then water washing the enzyme treated material immediately following completion of the enzyme treatment to a phytic acid concentration of less than 0.3% by weight of the resulting enzyme treated soy protein. Such embodiments include those nutritional formulas comprising the low-phytic acid soy protein isolates prepared in accordance with U.S. patent application 20020127288 (Wong et al.). Isolates prepared in accordance with such methods have been found to be unusually low in ash content, wherein the low ash content is characterized by reductions in minerals associated with the phytase treated soy protein such as manganese, phosphorus, aluminum, calcium, and so forth.

Although less preferred, the infant formulas of the present invention may further comprise other protein materials in addition to the soy-protein isolate component, provided that such other protein materials do not significantly increase the low phytic acid concentrations described herein. Such other protein materials may include intact and hydrolyzed proteins, free amino acids, and combinations thereof, non-limiting examples of which include hydrolyzed, partially hydrolyzed or non-hydrolyzed protein, and can be derived from any known or otherwise suitable source such as milk (e.g., casein, whey, lactose-free milk protein isolates), animal (e.g., meat, fish), cereal (e.g., rice, corn), or combinations thereof.

Non-limiting free amino acids suitable for use as such other protein materials include L-alanine, L-arginine, L-asparagine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-taurine, L-threonine, L-tryptophan, L-tyrosine, L-valine, and combinations thereof.

The present invention is also directed to those infant formula embodiments wherein the presence of the phytase-treated protein isolates is indirectly determined by a noted shift in polymeric ribonucleic acids (i.e., inherent RNA associated with soy protein) to monomeric units thereof. In this context, these embodiments will present as infant formulas having a TPAN (total potential available nucleosides) reduction of at least 75%, more typically at least about 90%, by weight relative to the TPAN concentration in a soy-based infant formula without any phytic acid reduction, e.g., protein isolate component having about 2.2% phytic acid by weight of the isolate. TPAN description, analysis, and detection are described, for example, by Leach et al., *Total Potentially Available Nucleosides of Human Milk by Stage of Lactation*, Am J Clin Nutr, 1995;61:1224-30 (1995).

Calcium Fortification

The infant formulas of the present invention comprise as an essential element a sufficient amount of calcium to meet the targeted nutritional needs of the infant, wherein the infant formula has a calcium to lipid weight ratio of less than 0.020, preferably from about 0.002 to about 0.020, more preferably from about 0.009 to about 0.018, more preferably from about 0.010 to about 0.017.

The calcium for use in the infant formulas can be derived from any known or otherwise effective nutrient source that provides the targeted calcium nutrition for the infant formulation. Non-limiting examples of suitable calcium sources includes inherent calcium from other nutrient or formula components, or as separately added calcium sources such as calcium citrate, calcium phosphate, or any other calcium source suitable for use in an infant formula.

Calcium concentrations in the infant formula will vary depending upon variables such as the nutritional needs of the targeted infant group as well as the desired product form, e.g., powder, ready-to-feed liquid, liquid concentrate. For ready-to-feed liquid formulations, the total calcium preferably ranges up to about 600 mg per liter of infant formula, more preferably from about 100 mg to about 550 mg, even more preferably from about 300 mg to about 540 mg, per liter of the infant formula. These calcium concentrations are based upon elemental calcium concentrations, i.e., calculated based on elemental calcium rather than the total weight of a calcium salt. These calcium concentrations can also be characterized per 100 kcal of the selected formula, at preferred levels of up to about 90 mg, more preferably from about 10 mg to about 85 mg, even more preferably from about 50 mg to about 80 mg, per 100 kcal of the infant formula.

It has been found that the infant formulas of the present invention can be formulated as calcium fortified, soy-based products, which result in optimal or improved stool softness when fed to infants, provided that the calcium fortification is maintained at the calcium to lipid weight ratios described herein. This was especially surprising since it is well known that both soy-based formulas and calcium fortification are known to increase the incidence of harder stool formation and even constipation in some individuals.

Optional Ingredients

The infant formulas of the present invention may further comprise other optional ingredients, either active or inactive, and includes those materials that may modify the physical, chemical, aesthetic or processing characteristics of the formulas or serve as pharmaceutical or additional nutritional components when used in the targeted population. Many such optional ingredients are known for use in food and nutritional products, including infant formulas, and may also be used in the infant formulas of the present invention, provided that such optional materials are compatible with the essential components described herein, are safe and effective for their intended use, and do not otherwise unduly impair product performance. Non-limiting examples of such optional ingredients include preservatives, anti-oxidants, emulsifying agents, pharmaceuticals, buffers, colorants, flavors, nucleotides and nucleosides, thickening agents, stabilizers, and other excipients or processing aids.

The infant formulas of the present invention preferably comprise any of a variety of vitamins, non-limiting examples of which include vitamin A, vitamin D, vitamin E, vitamin K, thiamine, riboflavin, pyridoxine, vitamin $B_{12}$, niacin, folic acid, pantothenic acid, biotin, vitamin C, choline, inositol, salts and derivatives thereof, and combinations thereof.

In addition to the calcium fortification described herein, the infant formulas may further comprise other minerals that are known or otherwise suitable for us in infant or other nutritional formulas, non-limiting examples of which include phosphorus, magnesium, iron, zinc, manganese, copper, iodine, sodium, potassium, chloride, selenium, and combinations thereof.

Selected embodiments of the present invention include those infant formulas that comprise per 100 kcal of formula one or more of the following: vitamin A (from about 250 to about 750 IU), vitamin D (from about 40 to about 100 IU), vitamin K (greater than about 4 μm), vitamin E (at least about 0.3 IU), vitamin C (at least about 8 mg), thiamine (at least about 8 μg), vitamin $B_{12}$ (at least about 0.15 μg), niacin (at least about 250 μg), folic acid (at least about 4 μg), pantothenic acid (at least about 300 μg), biotin (at least about 1.5 μg), choline (at least about 7 mg), and inositol (at least about 2 mg).

Selected embodiments of the present invention also include those infant formulas that comprise per 100 kcal of formula one or more of the following: phosphorus (at least about 25 mg), magnesium (at least about 6 mg), iron (at least about 0.15 mg), iodine (at least about 5 μg), zinc (at least about 0.5 mg), copper (at least about 60 μg), manganese (at least about 5 μg), sodium (from about 20 to about 60 mg), potassium (from about 80 to about 200 mg), chloride (from about 55 to about 150 mg) and selenium (at least about 0.5 mcg).

II. METHOD OF MAKING

The infant formulas of the present invention may be prepared by any known or otherwise effective technique, suitable for making and formulating the desired infant nutritional powder or liquid embodiment of the present invention, provided that the technique is appropriately modified so as to include the phytase-treated soy protein isolate component, and provided that the technique is appropriately modified to incorporate the other essential components as described herein.

For example, an appropriate quantity of phytase-treated soy-protein isolate can be dispersed or solubilized in water (or oil in combination with the oil soluble vitamins) to form a protein solution or liquid. The carbohydrate component of the desired formula (e.g., corn syrup solids, maltodextrins, sucrose) is dissolved or dispersed in water to form a carbohydrate solution or liquid. Appropriate minerals, including any added calcium-containing minerals, are dissolved or dispersed in water to form a mineral solution or liquid. Once formed, the three solutions or liquids (protein, carbohydrate, and mineral) are combined in appropriate quantities (or further combined where appropriate with oil in combination with oil soluble vitamins). This resulting combination is then heat-treated and homogenized (water soluble vitamins added following homogenization), packaged, and sterilized to form a liquid infant formula embodiment of the present invention, either as a ready-to-feed liquid or dilatable concentrate, depending upon the desired final ingredient concentrations. The homogenized liquids can also be spray dried (typically to a moisture content of 1.5-3.0%) and then packaged to form powder embodiments of the present invention.

The phytase-treated soy protein isolate for use in formulating the infant formulas of the present invention is preferably prepared in accordance with the methods disclosed U.S. patent application 20020127288 A1 (Wong et al.), wherein the methods provide a soy protein isolate containing little or no phytic acid within the concentration ranges defined herein. As one specific example of just such a method, two hundred forty-three pounds of a soy protein isolate is added to two thousand nine hundred and fifty-nine pounds of water to form a soy protein isolate slurry containing 7.6% solids. The pH of the slurry is adjusted to 4.5 with hydrochloric acid, and the temperature of the slurry is raised to 50° C. An enzyme preparation containing a suitable phytase enzyme, including phytase enzyme alone or in combination with acid phosphatase, having an activity of 1000 KPU/kg of curd solids is added to the slurry. Suitable commercial enzymes for this purpose include Natuphos® (BASF, Ludwigshafen, Germany), Finase® (Alko Ltd., Rajamaki, Finland), or other similar functioning phytase-containing enzyme systems. The slurry is treated with the enzyme preparation for two hours, after which the pH of the slurry is adjusted to 5.1 with a caustic blend of potassium hydroxide and sodium hydroxide. The slurry is then diluted with water to a concentration of 4.2% solids, and is washed in a bowl centrifuge. Two hundred and seventy-five pounds of the washed slurry are neutralized with a caustic blend of potassium hydroxide and sodium hydroxide. The neutralized material is heat treated by jet cooking at 150° C. and flash cooled to 53° C. by ejection into a vacuumized chamber having a pressure of about 26 torr. The heat treated slurry is then spray dried to recover 15.5 pounds of purified soy protein isolate for formulation into the infant formulas of the present invention.

The infant formulas of the present invention are most typically formulated to have or to otherwise provide upon dilution or reconstitution a caloric density of from about 19 to about 24 kcal/fl oz, more typically from about 20 to about 21 kcal/fl oz.

III. METHOD OF USE

The present invention is also directed to a method of providing infants with reduced incidence of constipation from a soy-based formula, as well as a method of providing infants with softer stools from a soy-based formula, wherein these methods comprise feeding the infants the calcium-fortified, soy-based, infant formula of the present invention. The present invention is also directed to a method of providing infants with daily nutrition and calcium fortification while reducing the incidence of constipation or excessively hard stool formation.

In the context of the methods of the present invention, the nutrition provided the infants can be used to meet their sole, primary, or supplemental nutritional needs. For powder embodiments, each method also includes the step of reconstituting the powder with an aqueous vehicle, most typically water or human milk, to form the desired caloric density, which is then orally or enterally fed to the infant to provide the desired nutrition. The powder is reconstituted with a quantity of water, or other suitable fluid such as human milk, to produce a volume suitable for about one feeding. Generally, from about 8 g to about 9 g of the nutritional powder are reconstituted with about 55 ml to about 65 ml of water to produce the desired nutrient density. The infant formula embodiments can be reconstituted or otherwise formulated to a variety of caloric densities, but will most typically have been reconstituted or formulated to a caloric density range of from about 19 to about 24 kcal/fl oz, more typically from about 20 to about 21 kcal/fl oz.

IV. EXAMPLES

The following examples illustrate specific embodiments of the infant formulas of the present invention, including methods of making the formulas, methods of using the formulas in providing daily nutrition with reduced incidence of constipation and/or excessively hard stool formation from a soy-based infant formula. The examples are given solely for the purpose of illustration and are not to be construed as limitations of the present invention, as many variations thereof are possible without departing from the spirit and scope of the invention.

Example 1

The following example illustrates a nutritional powder embodiment of the calcium fortified, soy-based, infant formulas of the present invention. The exemplified powder formula is described further in the following table.

TABLE 1.1

Example 1 - Powder Infant Formula

| Ingredient | Ingredient amount to formulate 100 kg of nutritional powder |
|---|---|
| Lipid | 28.0 kg |
| High oleic safflower oil | 11.5 kg |
| Soy bean oil | 8.1 kg |
| Coconut oil | 8.4 kg |
| Soy protein isolate[1] | 14.5 kg |
| Carbohydrate | 62.2 kg |
| Corn syrup | (52.0 kg) |
| Sucrose solids | (10.2 kg) |
| Minerals[2] | |
| Calcium phosphate | 1.8 kg |
| Sodium Chloride | 338 g |
| Magnesium chloride | 259 g |
| Potassium citrate | 1.05 kg |
| Potassium chloride | 191 g |
| Potassium iodide | 0.1 g |

TABLE 1.1-continued

Example 1 - Powder Infant Formula

| Ingredient | Ingredient amount to formulate 100 kg of nutritional powder |
|---|---|
| Vitamins | |
| Water soluble premix with trace minerals | 143 g |
| Oil soluble premix (ADEK) | 38 g |
| Methionine | 159 g |
| Vitamin C | 43.6 g |

[1] derived from phytase treated soy protein isolate with less than 0.2% phytic acid by weight of the isolate
[2] provides total 78 mg calcium per 100 kcal; calcium to lipid weight ratio of 0.014

The exemplified formula is prepared by first dispersing the carbohydrate (sucrose solids), and minerals in water with appropriate heat and agitation to form a carbohydrate-mineral slurry. The soy protein isolate is then dispersed in vegetable oil (soy, coconut, high oleic safflower) along with any oil soluble vitamins, emulsifiers, and antioxidants, with appropriate heat and agitation to form a protein-oil slurry. The formed slurries are then blended together with the corn syrup and the resulting pH adjusted to between 6.0 and 7.0 with an appropriate alkaline solution. Final total solid content of the resulting blend is 45-50.5%. The blend is then emulsified at 100-400 psi, subjected to high temperature steam treatment (HTST) at 160-170° F., and then homogenized using a 2-stage homogenization process at pressures of 900-1300 psi/400 psi. Water-soluble materials such as ascorbic acid and other water soluble vitamins, methionine, and trace minerals are then added to the homogenized mixture, which is then subjected to ultra high temperature (UHT) treatment at 220-250° F. The heat treated mixture is then cooled to 160-180° F. and spray dried at about 2300 psi at approximately 3 gal/min to yield a finished infant nutritional powder with a moisture content of 2-3% by weight of the powder.

Example 2

The following example illustrates a liquid embodiment of the calcium fortified, soy-based, infant formulas of the present invention. The exemplified formula is described further in the following table.

TABLE 2

Example 2 - Liquid Infant Formula

| Ingredient | Ingredient amount to formulate 100 kg of ready-to-feed nutritional liquid |
|---|---|
| Lipid | 3.65 kg |
| High oleic safflower oil | (1.4 kg) |
| Soy bean oil | (1.05 kg) |
| Coconut oil | (1.05 kg) |
| Soy protein isolate[1] | 1.9 kg |
| Carbohydrate | 8 kg |
| Corn syrup | (6.6 kg) |
| Sucrose solids | (1.4 kg) |
| Minerals[2] | |
| Potassium citrate | 65 g |
| Potassium chloride | 13.3 g |
| Magnesium chloride | 36.7 g |

TABLE 2-continued

Example 2 - Liquid Infant Formula

| Ingredient | Ingredient amount to formulate 100 kg of ready-to-feed nutritional liquid |
|---|---|
| Sodium chloride | 30.7 g |
| Calcium citrate | 165.1 g |
| Calcium phosphate | 114.3 g |
| Potassium phosphate | 98.3 g |
| Potassium iodide | 0.013 g |
| Vitamins | |
| Water soluble premix with trace minerals | 17.6 g |
| Oil soluble premix (ADEK) | 4.89 g |
| Methionine | 20.8 g |
| Vitamin C | 43.6 g |

[1] derived from phytase treated soy protein containing less than 02% phytic acid by weight of the isolate
[2] provides total 78 calcium per 100 kcal; calcium to lipid weight ratio of 0.014

The exemplified formula is prepared by first dispersing the carbohydrate (sucrose solids), and minerals in water with appropriate heat and agitation to form a carbohydrate-mineral slurry. The soy protein isolate is then dispersed in vegetable oil (soy, coconut, high oleic safflowerl) along with any oil soluble vitamins, emulsifiers, and antioxidants, with appropriate heat and agitation to form a protein-oil slurry. The formed slurries are then blended together with corn syrup and the resulting pH adjusted to between 6.0 and 7.0 with an appropriate alkaline solution. Final total solid content of the resulting blend is 20-30%. The blend is then emulsified at 100-500 psi, subjected to high temperature steam treatment (HTST) at 143-154° C., and then homogenized using a 2-stage homogenization process at pressures of 3000-4000 psi/500 psi. Water-soluble materials such as ascorbic acid and other water soluble vitamins, methionine, and trace minerals are then added to the homogenized mixture. The mixture is diluted with water to a solid content of 12-13%, packaged and sealed into appropriate containers, and then sterilized at 115-126° C.

Clinical Data

A study was conducted to evaluate infants using one of three different calcium-fortified, soy-based, infant formulas. The primary objective of the study was to evaluate and compare stool consistency for term infants aged 1-3 months fed one of three test formulas for a defined period of time.

The three test formulas were: Formula 1) Isomil® brand soy-based infant formula, commercially available from Ross Products Division, Abbott Laboratories, Columbus, Ohio, USA, Formula 2) soy-based infant formula containing soy protein isolates dephytinized by a phytase treatment method, and Formula 3) soy-based infant formula containing soy protein isolates dephytinized by an ion exchange method.

Each of the three study formulas has a caloric density of 20 kcal/fl oz and is prepared as a packaged, ready-to-feed liquid. The formulas are described below in Table 3.1. Ingredient amounts listed in the table are per liter of the study formula.

TABLE 3.1

Infant Formulas for Clinical Study

| Ingredient | Formula 1 Control Part I | Formula 1 Control Part II | Formula 2 Ion Exchange | Formula 3 Phytase wash |
|---|---|---|---|---|
| PROTEIN - g | 17.4 | 17.1 | 16.6 | 17.5 |
| Soy protein isolate | | | | |
| FAT - g | 36.6 | 37.0 | 37.0 | 36.4 |
| Coconut, soy, high oleic safflower (30/30/40 blend) | | | | |
| Coconut oil | 30% | 30% | 30% | 30% |
| Soy oil | 30% | 30% | 30% | 30% |
| High oleic safflower oil | 40% | 40% | 40% | 40% |
| CARBOHYDRATE - g | 68.9 | 68.0 | 68.0 | 68.5 |
| Corn syrup | 60% | 60% | 80% | 80% |
| Sucrose | 40% | 40% | 20% | 20% |
| MINERALS: | | | | |
| Calcium - mg | 822 | 829 | 530 | 522 |
| Phosphorus - mg | 499 | 538 | 300 | 292 |
| Magnesium - mg | 60.5 | 59.4 | 50 | 60.5 |
| Sodium - mg | 286 | 345 | 410 | 514 |
| Potassium - mg | 931 | 1010 | 730 | 1081 |
| Chloride - mg | 428 | 465 | 410 | 514 |
| Iron - mg | 12.3 | 13.5 | 12.5 | 15.0 |
| Zinc - mg | 5.1 | 5.1 | 5.1 | 5.1 |
| Copper - mg | 0.51 | 0.51 | 0.51 | 0.51 |
| Iodine - mg | 0.088 | 0.165 | 0.100 | 0.090 |
| Manganese - μg | 200 | 200 | 200 | 200 |
| Selenium - μg | 11 | 11 | 11 | 11 |
| VITAMINS: | | | | |
| A - IU | 2645 | 2957 | 2200 | 2635 |
| D - IU | 400 | 400 | 400 | 400 |
| E - IU | 18.0 | 21.9 | 20.7 | 21.4 |
| K - μg | 100 | 100 | 100 | 100 |
| C - mg | 163 | 214 | 90 | 103 |
| Thiamin - mg | 1.53 | 1.67 | 0.58 | 1.51 |
| Riboflavin - mg | 0.60 | 0.60 | 0.60 | 0.60 |
| Pyridoxine - mg | 0.621 | 0.56 | 0.54 | 0.602 |
| B12 - μg | 3.6 | 3.6 | 3.6 | 3.6 |
| Niacin - mg | 9.1 | 9.1 | 9.1 | 9.1 |
| Folic acid - μg | 100 | 100 | 100 | 100 |
| Pantothenic acid - mg | 5.0 | 5.0 | 5.0 | 5.0 |
| Biotin - μg | 30 | 30 | 30 | 30 |
| Taurine - mg | 45 | 45 | 45 | 45 |
| Choline (total) - mg | 118 | 54 | 54 | 54 |
| Inositol - mg | 34 | 34 | 34 | 34 |
| Beta-carotene - μg | 536 | 400 | 400 | 400 |
| L-carnitine - mg | 15.1 | 11 | 11 | 11 |
| L-methionine - mg | 171 | 194 | 193 | 192.4 |
| OTHER: | | | | |
| Phytic acid[1] | 0.418 g | 0.418 g | 0.019 g | 0.019 g |
| Calcium:lipid wt ratio | 0.0224 | 0.0224 | 0.0143 | 0.0143 |

[1] phytic acid from added soy protein isolate

Ingredient Listing of Study Infant Formulas

Formula 1: Water, corn syrup, sucrose, soy protein, isolate, high oleic safflower oil, coconut oil, soy oil, calcium citrate, calcium phosphate tri-basic, potassium citrate, potassium phosphate mono-basic, potassium chloride, mono- and diglycerides, soy lecithin, magnesium chloride, carrageenan, ascorbic acid, L-methionine, potassium phosphate dibasic, sodium chloride, choline chloride, ferrous sulfate, taurine, m-inositol, alpha-tocopheryl acetate, zinc sulfate, L-carnitine, niacinamide, calcium pantothenate, cupric sulfate, vitamin A palmitate, beta carotene, thiamine chloride hydrochloride, riboflavin, pyridoxine hydrochloride, folic acid, manganese sulfate, phylloquinone, potassium iodide, biotin, sodium selenate, vitamin D3 cyanocobalamin and beta carotene.

Formula 2: Water, corn syrup, sucrose, dephytinized soy protein isolate (ion exchange), high oleic safflower oil, coconut oil, soy oil, calcium citrate, calcium phosphate tri-basic, potassium citrate, potassium phosphate monobasic, potassium chloride, mono- and diglycerides, soy lecithin, magnesium chloride, carrageenan, ascorbic acid, L-methionine, potassium phosphate dibasic, sodium chloride, choline chloride, ferrous sulfate, taurine, m-inositol, alpha-tocopheryl acetate, zinc sulfate, L-carnitine, niacinamide, calcium pantothenate, cupric sulfate, vitamin A palmitate, beta carotene, thiamine chloride hydrochloride, riboflavin, pyridoxine hydrochloride, folic acid, manganese sulfate, phylloquinone, potassium iodide, biotin, sodium selenate, vitamin D3 cyanocobalamin and beta carotene.

Formula 3: Water, corn syrup, sucrose, dephytinized soy protein isolate (phytase treatment), high oleic safflower oil, coconut oil, soy oil, calcium citrate, calcium phosphate tri-basic, potassium citrate, potassium phosphate monobasic, potassium chloride, mono- and diglycerides, soy lecithin, magnesium chloride, carrageenan, ascorbic acid, L-methionine, potassium phosphate dibasic, sodium chloride, choline chloride, ferrous sulfate, taurine, m-inositol, alpha-tocopheryl acetate, zinc sulfate, L-carnitine, niacinamide, calcium pantothenate, cupric sulfate, vitamin A palmitate, beta carotene, thiamine chloride hydrochloride, riboflavin, pyridoxine hydrochloride, folic acid, manganese sulfate, phylloquinone, potassium iodide, biotin, sodium selenate, vitamin D3 cyanocobalamin and beta carotene.

Study Design

The study was a randomized, masked, crossover study of stool characteristics in which term infants were randomized upon entry into one of two feeding sequences. For the first sequence, referred to herein as Part I, infants were fed either Formula 1 (commercial soy formula) or Formula 2 (soy formula with soy protein isolate from ion exchange dephytinization) for 7 days each in a crossover design. Upon successful completion of Part 1 of the study by the 12 subjects enrolled according to criteria, enrollment continued into one of two additional feeding sequences until successful completion of Part II by 12 more subjects.

In Part II of the study, infants were fed either Formula 1 (commercial soy formula) or Formula 3 (soy formula with soy protein isolate derived from phytase dephytinization). These Formulas 1 and 3 were also fed for 7 days each in a cross-over design. Parents or caregivers recorded stool characteristics and volume of intake during each study period and responded to an Infant Feeding and Stool Patterns Questionnaire at the end of each period.

The three formulas used in the study were similar in that each contained a soy protein isolate and each was calcium fortified (see Table 3.1). The formulas were also similar with respect to many of the other added nutrients or formula components, except that Formula 1 had a calcium to lipid weight ratio of 0.0224 whereas Formulas 2 and 3 had calcium to lipid ratios of 0.014. In further contrast, Formula 1 had a conventional soy protein isolate with a phytic acid concentration of 0.418 g per liter, whereas Formulas 2 and 3 were dephytinized by ion exchange and phytase treatment methods, respectively, with resulting phytic acid concentrations of only 0.019 g per liter.

Inclusion Criteria

Equal numbers of full term, healthy, infants ages 28-56 days or 57-84 days with a birth weight of 2,500 g or greater were enrolled upon written consent from a parent or legal representative. Infants were to have had no known prior history of intolerance to a soy-based formula and were not to have received antibiotics for 1 week prior to study entrance by parental report. See the following Table 3.2 for disposition of infants enrolled in the study.

TABLE 3.2

Disposition of Study Participants

| | Feeding Group | | Number of Infants |
|---|---|---|---|
| | Study Period 1 | Study Period 2 | |
| Part I: Formula 1 (F1) vs. Formula 2 (F2) | F1 → F2 (n = 6) | F2 → F1(n = 8) | 14 |
| Infants Ages 28-56 days | 3 | 4 | 7 |
| Infants Ages 57-84 days | 3 | 4 | 7 |
| Withdrew from protocol | 0 | 2 | 2* |
| Complete protocol | 6 | 6 | 12 |
| Part II: Formula 1 (F1) vs. Formula 3 (F3) | F1 → F3 (n = 9) | F3 → F1 (n = 7) | 16 |
| Infants Ages 28-56 days | 5 | 4 | 9 |
| Infants Ages 28-56 days | 4 | 3 | 7 |
| Withdrew from protocol | 3 | 1 | 4** |
| Complete protocol | 6 | 6 | 12 |

*Infants 1) withdrawn after 1 day for an unrelated surgery; and 2) withdrawn after 1 day due to constipation
**Infants: 1) withdrawn due to fussiness, crying, screaming; 2) withdrawn due to loose stools, refusing formula; 3) withdrawn after failure to keep study visit appointment; 4) withdrawn when hospitalized with respiratory syncytial virus.

Study Variables and Main Outcome Measure

The primary outcome variable was stool consistency. This variable was evaluated and reported for each participant and the corresponding study groups, as an average mean rank stool consistency (MRSC) value. The MRSC scoring and evaluation system is well known in the infant formula arts, and is based upon a 1-5 scale (1-watery, 2-loose, 3-soft, 4-formed, 5-hard).

Test Formulas

The focus of the study were the two dephytinized infant formulas-Formulas 2 derived from soy protein isolates dephytinized by ion exchange, and Formula 3 derived from soy protein isolates dephytinized by phytase treatment. Formulas 2 and 3 had similar calcium concentrations (530 mg/L) and calcium to lipid weight ratios (0.0143), whereas Formula 1 (commercial soy formula as control) had a higher calcium concentration (700 mg/L) and a higher calcium to lipid weight ratio (0.0224).

Study Results

Results of the study are summarized and in the following Tables 3.3 and 3.4.

TABLE 3.3

Part I Study Results

| Formula 1 v. Formula 3 | Formula 2 Ion exchange | Formula 1 Control | p-Value |
|---|---|---|---|
| Mean Rank Stool Consistency | | | |
| Infants ages 28-56 days | 3.10 | 3.28 | 0.5212 |
| Infants ages 57-84 days | 2.82 | 3.38 | 0.192 |
| Predominant Stool Consistency | | | |
| Infants ages 28-56 days | 2.17 | 2.50 | 0.3739 |
| Infants ages 57-84 days | 2.40 | 3.00 | 0.3333 |
| Stool Frequency | | | |
| Infants ages 28-56 days | 1.28 | 1.53 | 0.4392 |
| Infants ages 57-84 days | 2.11 | 1.61 | 0.4998 |

TABLE 3.4

Part II Study Results

| Formula 1 v. Formula 3 | Formula 3 Phytase Treatment | Formula 1 Control | p-Value |
|---|---|---|---|
| Mean Rank Stool Consistency | | | |
| Infants ages 28-56 days | 2.33 | 2.72 | 0.0885 |
| Infants ages 57-84 days | 2.45 | 3.10 | 0.0055 |
| Predominant Stool Consistency | | | |
| Infants ages 28-56 days | 2.5 | 2.7 | 0.5185 |
| Infants ages 57-84 days | 2.2 | 3.2 | 0.1447 |
| Stool Frequency | | | |
| Infants ages 28-56 days | 1.39 | 1.47 | 0.2254 |
| Infants ages 57-84 days | 1.22 | 1.56 | 0.2582 |

Part I: Formula 1 versus Formula 2—Mean rank stool consistency (MRSC) did not differ significantly between the Formula 1 and Formula 2 feeding groups. The MRSC for Formula 1 groups was 3.28 for the younger infants and 3.38 for the older infants. The MRSC for the Formula 2 groups was 3.10 for the younger infants and 2.82 for the older infants.

Part II: Formula 1 and Formula 3—MRSC was significantly looser (p=0.0055) when older infants were fed Formula 3 (MRSC 2.45) rather than Formula 1 (MRSC 3.10), and borderline significant for younger infants fed Formula 3 (MRSC 2.33) rather than Formula 2 (MRSC 2.72).

CONCLUSIONS

It can be seen from the study results (see Tables 3.3 and 3.4) that the soy-based formulas derived from phytase treated protein isolates (Formula 3) produced softer stools as compared to a commercial soy formula (Formula 1). A similar benefit was not realized with the soy-based formula derived from ion exchanged protein isolates (Formula 2).

The results of the study were surprising. The study shows that a soy-based infant formula can now be formulated and used in infants to reduce the incidence of constipation or hard stool formulation, a problem often associated with the use of many soy-based infant formulas. It is now believed that the softer stools resulting from the use of Formula 3 as compared to the use of either Formula 1 or Formula 2 was the direct result of the Formula 3 calcium to lipid ratio of less than about 0.020, and the use of a soy protein isolate dephytinized by phytase or phytase-functioning enzymes. Dephytinization by ion exchange, surprisingly, did not produce the same significant result.

What is claimed is:

1. A method of softening infant stools, said method comprising:
   (A) treating a soy protein material with a phytase-containing enzyme and then water washing the enzyme treated material immediately following completion of the enzyme treatment to a phytic acid concentration of less than about 0.3% by weight of the resulting enzyme treated soy protein,
   (B) preparing an infant formula containing
      (i) from about 2.0% up to about 5.4% by weight of lipid,
      (ii) from about 5.4% to about 10.8% by weight of carbohydrate,
      (iii) from about 0.7% to about 2.4% by weight of the water-washed, phytase-treated soy protein, and
      (iv) from about 10 mg to about 600 mg of calcium per liter to form a calcium to lipid weight ratio within the formula of from about 0.002 to about 0.020, and then
   (C) feeding the formula to an infant resulting in a reduced mean rank stool consistency as compared to a control soy formula without water-washed, phytase treated soy.

2. The method of claim 1 wherein the formula comprises from about 2.7% to about 4.5% by weight of lipid, from about 6.1% to about 8.8% by weight of carbohydrate, and from about 1.0% to about 2.3% by weight of phytase-treated soy protein.

3. The method of claim 1 wherein the formula comprises from about 300 mg to about 550 mg of calcium per liter.

4. The method of claim 1 wherein the weight ratio of the calcium to the lipid is from about 0.010 to about 0.017.

5. The method of claim 1 wherein the formula contains not more than about 1.4 mg phytic acid per 100 kcal of formula.

6. The method of claim 1 wherein the water-washed, phytase-treated soy protein contains less than about 0.05% by weight of phytic acid.

* * * * *